(12) United States Patent
Comeau et al.

(10) Patent No.: US 7,442,552 B2
(45) Date of Patent: *Oct. 28, 2008

(54) PRESSURIZED OXYGEN FOR EVALUATION OF MOLDING COMPOUND STABILITY IN SEMICONDUCTOR PACKAGING

(75) Inventors: Joseph K. V. Comeau, Essex Junction, VT (US); Adele M. Mahoney, Underhill, VT (US); Jason P. Ritter, Jericho, VT (US); Gerald J. Scilla, Essex Junction, VT (US); Charles H. Wilson, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/861,369

(22) Filed: Sep. 26, 2007

(65) Prior Publication Data
US 2008/0006079 A1      Jan. 10, 2008

Related U.S. Application Data

(63) Continuation of application No. 10/658,859, filed on Sep. 9, 2003, now Pat. No. 7,300,796.

(51) Int. Cl.
*G01N 31/00* (2006.01)
(52) U.S. Cl. .................. 436/1; 436/103; 436/127
(58) Field of Classification Search ............... 436/1, 436/103, 127, 161, 181; 422/83; 73/37
See application file for complete search history.

(56) References Cited

U.S. PATENT DOCUMENTS

| | | | |
|---|---|---|---|
| 3,421,856 A | 1/1969 | Stenger et al. | |
| 3,578,756 A | 5/1971 | Evans et al. | |
| 3,820,379 A | 6/1974 | Nelson et al. | |
| 4,758,408 A | 7/1988 | Krawetz et al. | |
| 4,942,750 A | 7/1990 | Conaway | |
| 4,990,312 A | 2/1991 | Rucker et al. | |
| 6,858,300 B2 | 2/2005 | Kinose et al. | |
| 7,098,276 B1 | 8/2006 | Kiuchi et al. | |
| 7,300,796 B2 * | 11/2007 | Comeau et al. | 436/1 |

FOREIGN PATENT DOCUMENTS

JP         2003-40609         2/2003

* cited by examiner

*Primary Examiner*—Maureen M Wallenhorst
(74) *Attorney, Agent, or Firm*—Schmeiser, Olsen & Watts; Todd M. C. Li

(57) ABSTRACT

A test environment and an associated method of testing and analyzing a semiconductor package material containing a molding compound, for stability in a sustained oxygen environment. Test samples are exposed to a pressurized gas containing oxygen, under elevated temperature below the glass transition temperature of the molding compound. Control samples are exposed to a pressurized inert gas under similar or more severe conditions of gas pressure, temperature, and humidity. At least one characteristic common to the test samples and the control samples is measured. A determination is made as to whether there exists at least one significant difference between the at least one measured characteristic of the test samples and the control samples.

3 Claims, 5 Drawing Sheets

| # | PACKAGE TYPE | FIELD ISSUE? | PHOSPHATE EXTRACT ($\mu g/mm^2$) | | CHLORIDE EXTRACT ($\mu g/mm^2$) | |
|---|---|---|---|---|---|---|
| | | | OXYGEN GAS | NITROGEN GAS | OXYGEN GAS | NITROGEN GAS |
| 1 | QFP#1 WITH RED PHOSPHORUS FLAME RETARDANT | YES | 1.506 | 0.04 | 0.050 | 0.003 |
| 2 | QFP#2 WITH RED PHOSPHORUS FLAME RETARDANT | YES | 1.313 | 0.007 | 0.070 | 0.001 |
| 3 | PBGA WITH RED PHOSPHORUS FLAME RETARDANT | SUSPECT | 0.977 | <0.002 | 0.051 | 0.001 |
| 4 | SOIC WITH RED PHOSPHORUS FLAME RETARDANT | YES | 0.814 | 0.08 | 0.030 | <0.001 |
| 5 | QFP#3 WITH RED PHOSPHORUS FLAME RETARDANT | SUSPECT | 0.137 | <0.002 | 0.011 | 0.000 |
| 6 | QFN WITH ORGANIC P AS CATALYST AND ORGANIC FLAME RETARDANT | NO | 0.002 | <0.002 | 0.003 | <0.001 |
| 7 | QFP - Sb/Br FLAME RETARDANT & ORGANIC P AS CATALYST | NO | <0.002 | <0.002 | <0.001 | 0.001 |
| 8 | PBGA WITH ORGANIC P AS CATALYST | NO | <0.002 | <0.002 | 0.001 | 0.001 |
| 9 | QFP WITH ORGANIC P AS CATALYST & ORGANIC FLAME RETARDANT | NO | <0.002 | <0.002 | <0.001 | 0.001 |
| 10 | FC PBGA ORGANIC P AS CATALYST | NO | <0.002 | <0.002 | 0.002 | <0.001 |

QFP = QUAD FLATPACK (WIREBOND)
PBGA = PLASTIC BALL GRID ARRAY (WIREBOND)
SOIC = SMALL OUTLINE INTEGRATED CIRCUIT (WIREBOND)
QFN = QUAD FLATPACK NO LEAD (WIREBOND)
FCPBGA = FLIP CHIP PLASTIC BALL GRID ARRAY (FLIP CHIP)

*FIG. 1*

PRESSURIZED OXYGEN FOR EVALUATION OF MOLDING COMPOUND STABILITY IN SEMICONDUCTOR PACKAGING

This application is a Continuation of Ser. No. 10/658,859, filed Sep. 9, 2003, now U.S. Pat. No. 7,300,796 issued on Nov. 27, 2007.

BACKGROUND OF THE INVENTION

1. Technical Field

The present invention relates to a test environment and an associated method of testing and analyzing a semiconductor package material for stability in a sustained oxygen environment.

2. Related Art

A serious industry-wide problem is known to exist with semiconductor packages having an epoxy molding compound that includes an elemental red phosphorus-based flame retardant additive. After about two and a half years in the field, some of the semiconductor packages and materials therein failed, such as by developing electrical shorts, particularly during summer months during periods of high temperature and humidity. In efforts to understand why the fails occurred, the packaging material with red phosphorus was subjected to extensive testing by various interested parties, including conventional accelerated stress tests, tests involving exposure to humidity, elevated temperature, and voltage, etc. Unfortunately, the preceding tests demonstrated acceptable performance and therefore did not provide any insight as to why the aforementioned fails have been occurring with the semiconductor packages. The nature of this problem and the lack of insight into why this problem exits, as well as adverse consequences of this problem including the filing of multiple lawsuits, are discussed in "Nikkei Electronics" (Oct. 21, 2002). At present, there is no publicly available information that sheds light as to why the aforementioned fails have been occurring.

Accordingly, there is a need for a method of testing and analysis, as well as an associated test environment, that leads to detection and minimization of potential failure mechanisms in semiconductor packages containing potentially unstable materials such as red phosphorus.

SUMMARY OF THE INVENTION

The present invention provides a method of testing a semiconductor packaging material containing a molding compound for stability of the semiconductor packaging material in a sustained oxygen environment, said method comprising:

providing N substantially identical samples such that N is a positive integer of at least 2, wherein each of the N samples comprises the semiconductor packaging material, wherein T samples of the N samples are test samples, wherein C samples of the N samples are control samples, and wherein T and C are positive integers such that T+C=N;

exposing during a time period $\tau$ the T test samples to a pressurized gas having a total pressure $P_{TOT}(t)$, said pressurized gas comprising oxygen gas, wherein for times t during $0 \leq t \leq \tau$ the oxygen gas has a partial pressure $P(t)$ of at least $P_1$ and a temperature $T(t)$ satisfying $T_G - \Delta T_2 \leq T(t) \leq T_G - \Delta T_1$ such that $0 < \Delta T_1 \leq \Delta T_2$ for glass transition temperature $T_G$ of the molding compound, wherein during $0 \leq t \leq \tau$ the T test samples are exposed to moisture having a relative humidity $H(t)$ such that $H_1 \leq H(t) \leq H_2$, wherein $H_1 \geq 0\%$ and $H_2 \leq 100\%$, wherein $\tau$ is at least about 12 hours, wherein $P_1$ is about 15 psi, and wherein $T_G - \Delta T_2$ is at least about 20° C.; and exposing the C control samples during times t for a time period $\tau'$ to a pressurized inert gas having a pressure $P'(t)$ and a temperature of $T'(t)$ at a relative humidity $H'(t)$, wherein a common time interval exists for times t during which both the pressurized gas comprising oxygen and the pressurized inert gas are being exposed by the respective exposing steps, wherein during said common time interval: $P'(t) \geq P(t)$ or $P'(t)$ does not substantially differ from $P(t)$, $T'(t) \geq T(t)$ or $T'(t)$ does not substantially differ from $T(t)$, and $H'(t) \geq H(t)$ or $H'(t)$ does not substantially differ from $H(t)$.

The method may further comprise (after said exposing the T test samples and the C control samples):

measuring at least one characteristic common to the C control samples and the T test samples; and determining whether there exists at least one significant difference between the at least one measured characteristic of the T test samples and the at least one characteristic of the C control samples.

The present invention provides a test environment, comprising a chamber containing S samples, a pressurized gas, and moisture, wherein the S samples each comprise a semiconductor packaging material that includes a molding compound, wherein S is at least 1 and if S>1 then the S samples are substantially identical, wherein the S samples are being exposed to the pressurized gas and the moisture, wherein the pressurized gas includes at least one of oxygen gas and an inert gas, wherein the pressurized gas has a temperature T satisfying $T_G - \Delta T_2 \leq T \leq T_G - \Delta T_1$ such that $0 < \Delta T_1 \leq T_2$ for glass transition temperature $T_G$ of the molding compound, wherein the moisture has a relative humidity H such that $H_1 \leq H \leq H_2$, wherein $H_1 \geq 0\%$ and $H_2 \leq 100\%$, wherein $T_G - \Delta T_2$ is at least about 20° C., wherein if the pressurized gas includes the oxygen gas then the partial pressure of the oxygen gas is at least about 15 psi, and wherein if the pressurized gas does not include the oxygen gas then the pressure of the inert gas is at least about 15 psi.

The present invention provides a method of testing and analysis, as well as an associated test environment, that prevents or reduces fails relating to semiconductor packages having a molding compound material that contains red phosphorus.

BRIEF DESCRIPTION OF THE DRAWINGS

FIG. 1 is a table depicting phosphate and chloride ion extraction concentrations from semiconductor packages that had been subjected to pressurized oxygen and pressurized nitrogen, in accordance with embodiments of the present invention.

DETAILED DESCRIPTION OF THE INVENTION

Figure 2A:
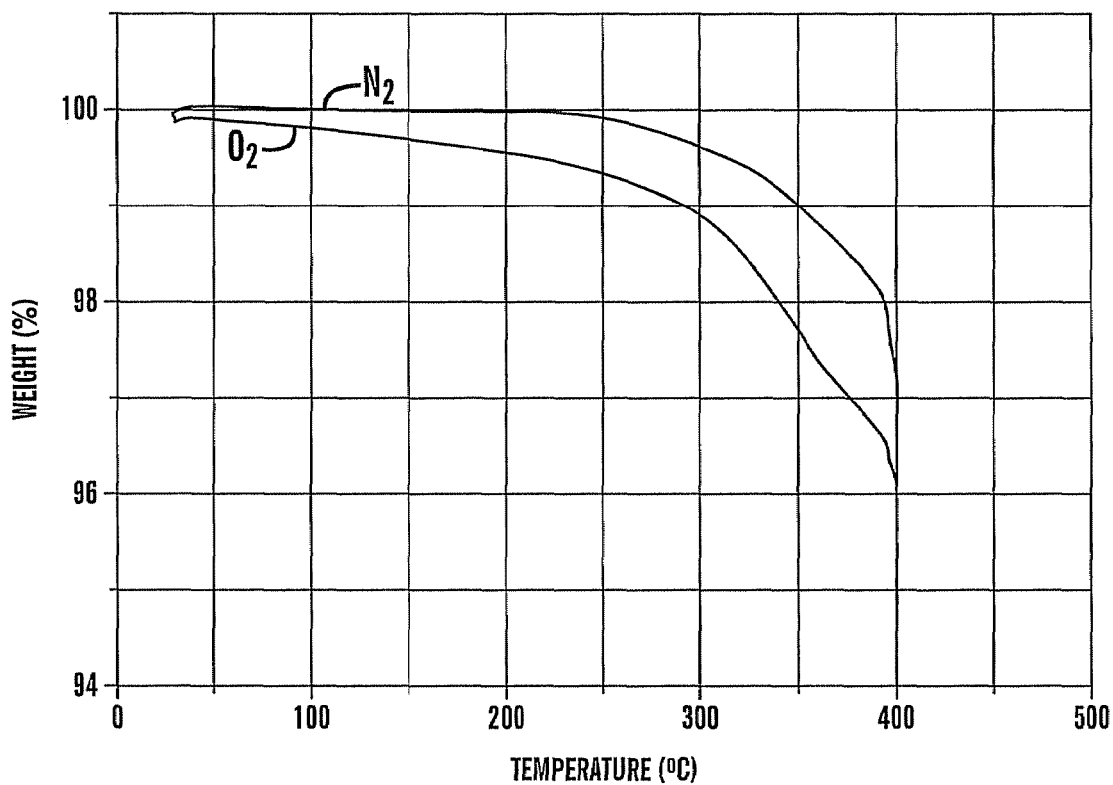
FIGS. 2A and 2B are thermogravimetric graphical profiles for semiconductor packages that had been subjected to pressurized oxygen and pressurized nitrogen, in accordance with embodiments of the present invention.

As explained supra in the Related Art section, there is no publicly available information that sheds light as to why the fails, including electrical shorts, have been occurring with semiconductor packages which include molding compound material containing red phosphorus. A molding compound of a semiconductor package is defined herein, including in the claims, as a thermosetting plastic for packaging of semiconductors. Properties of the molding compound include suitable dielectric strength, arc resistance, dry insulation resistance, low dielectric constant, dimensional stability, low flammability, and ease of molding. Examples of molding compound classes that may exist in semiconductor packages include alkyds, aminos, diallyl phthalates, epoxies, fluoropolymers, phenolics, polyesters and rigid silicones.

In response to this problem, the inventors of the present invention have performed experiments that explain the root cause of this problem. Based on the results of said experiments, the inventors of the present invention have formulated a test and analysis methodology, and an associated test environment, for preventing or reducing adverse consequences (e.g., electrical shorts) associated with this problem. Accordingly, said experiments will be next described, followed by a description of the test and analysis methodology, and an associated test environment, of the present invention.

EXPERIMENTS

The inventors of the present invention hypothesized that oxygen could be the root cause of the problem, through interaction between oxygen and phosphorus in the presence of moisture. The present inventors tested this hypothesis, by subjecting the packaging material to a 100% pressurized oxygen environment at elevated temperature and humidity to accelerate the reaction. In particular, the tests were performed at 1800 psi oxygen pressure at 85° C. (which is below the glass transition temperature of the molding compound of the packaging material) for at least 4 days, which provides acceleration of about 600 times the normal reaction with oxygen at room temperature and atmosphere concentrations of oxygen. These results showed that the packaging material broke down, and large quantities of phosphates were extractable from the molding compound following the testing. The experimental results demonstrated that the oxygen reacted with phosphorus in the presence of moisture to generate phosphoric acid. Follow-up experimentation (i.e., electrical testing, material property testing, thermogravimetric analysis) showed that the properties of the molding compound had changed and that electrical shorts were generated. The experimental results correlated with observations of similar or comparable packaging materials in the field (i.e., semiconductor package types that failed in the field also tended to fail in the experiments, whereas semiconductor package types that did not fail in the field also tended not to fail in the experiments). The experimental results support a mechanism of phosphoric acid generation, wherein the generated phosphoric acid provides an electrolyte path for the migration of copper ions under an applied voltage bias, and wherein the copper ions result from the dissolving of copper in the phosphoric acid. Thus the electrical shorts were caused by the migration of the copper ions in the phosphoric acid generated by the chemical reaction of phosphorus and oxygen in the presence of moisture.

FIGS. 1 and 2, which summarize a portion of the experimental results, are next described.

FIG. 1 is a table that lists ion extracts of phosphate ions and chloride ions, obtained from ion chromatography of ten different semiconductor packages (identified in the "Package Type") which were each subjected to pressurized oxygen at 1800 psi partial pressure of oxygen for 4 days at a temperature of 85° C. subject to moisture contact at a relative humidity of 100%. From 1 to 8 samples were used for each semiconductor package type. During the exposure to pressurized oxygen, the packages were in an open vial in a closed, heated chamber. Following the exposure to the pressurized oxygen, about 25 milliliters of deionized water was added to the vial and the packages were soaked in the deionized water for 24 hours; then the deionized water was analyzed by ion chromatography to determine the type and concentration of ions extracted from the package into the deionized water.

The temperature of 85° C. is high enough to accelerate the reaction with oxygen, but is less than the glass transition temperature of the molding compound that is within any of the ten packages tested, in order to reduce or minimize the chance of stress relief from material properties that exist in the molding compound at $T_G$ or above.

The ten different semiconductor packages were also subject to pressurized nitrogen as a control, at the same gas pressure, temperature, and moisture content as existed with the oxygen gas. One or more samples were used for each package type. Thus, FIG. 1 has an "Oxygen Gas" column and a "Nitrogen Gas" column for both the phosphate ion extract data and the chloride ion extract data. The ion extract data, averaged over the samples for each package type, is expressed in units of micrograms per square millimeter of package surface. The "Field Issues?" column identified whether electrical fails (i.e., shorts) had been observed in the field for each type of module (i.e., "yes" means that electrical fails have been observed, while "no" means that electrical fails have not been observed). Package types 1-5 included a molding compound comprising red phosphorus, while package types 6-10 included a molding compound not containing red phosphorus but containing phosphorus in the form of an organic phosphorus compound.

FIG. 1 shows that negligible amounts of phosphate ions and chloride ions were extracted when pressurized nitrogen gas was used, which is as expected since nitrogen gas is inert and is therefore not expected to chemically react with any packaging material.

The extracted phosphate shown in FIG. 1 is significantly higher for the pressurized oxygen environment than for the pressurized nitrogen environment for packages 1-5, which correlates with the fact that packages 1-5 each have a red phosphorus-containing molding compound and also with the fact that package types 1-5 have known or suspected field issues. The extracted phosphate has a concentration ranging from 0.15 to 2.5 $\mu g/mm^2$ for packages 1-5, which correlates with the fact that packages known to have had problems in the field had ion concentrations of the order of 0.1 $\mu g/mm^2$ or higher. Thus, a measured phosphate concentration of at least 0.1 $\mu g/mm^2$ (or a more conservative phosphate concentration of at least 0.05 $\mu g/mm^2$) may be a useful threshold for detection of an oxygen reaction problem. In contrast, packages 6-10 show no statistically significant difference in extracted phosphate for the pressurized oxygen environment as compared with the pressurized nitrogen environment, which correlates with the fact that packages 6-10 each lack red phosphorus (but contain phosphorus bound in an organic phosphorus compound) and also with the fact that package types 6-10 have no known field issues.

The extracted chloride shown in FIG. 1 is significantly higher for the pressurized oxygen environment than for the pressurized nitrogen environment for packages 1-5, which again correlates with the fact that packages 1-5 each have a red phosphorus-comprising molding compound and also with the fact that package types 1-5 have known or suspected field issues. The extracted chloride has a concentration ranging from 0.01 to 0.07 $\mu g/mm^2$ for packages 1-5. In contrast, packages 6-10 show no significant difference in extracted chloride for the pressurized oxygen environment as compared with the pressurized nitrogen environment, which again correlates with the fact that packages 6-10 each have a red phosphorus-free molding compound and also with the fact that package types 6-10 have no known field issues. Although there is no expected chemical reaction involving chloride, increased porosity of packaging material resulting from the reactions between oxygen and phosphorus provides migration paths for chloride ions already present in the semiconductor packages, which accounts for the aforementioned chloride ion concentrations detected by the ion chromatography.

Figure 2B:
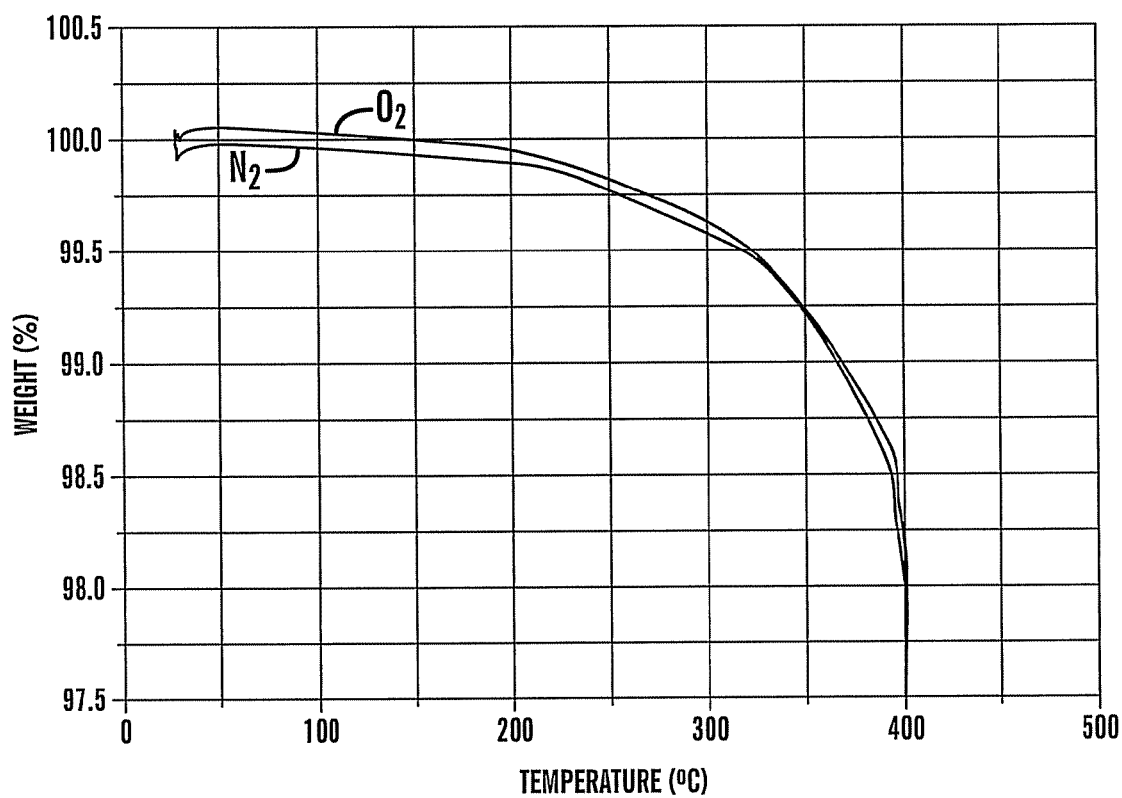

FIG. 2A depicts a thermogravimetric profile of package #2 of FIG. 1, while FIG. 2B depicts a thermogravimetric profile of package #9 of FIG. 1. The package of FIG. 2A contained inorganic red phosphorus (as in the table of FIG. 1, #2), while the package of FIG. 2B did not contain red phosphorus but contained phosphorus in a bound form in organic phosphorus compounds (FIG. 1 #9). In both FIGS. 2A and 2B, the package sample was subjected to a gas pressure of 1800 psi and a temperature of 85° C. for 4 days. The relative humidity was 100% in FIG. 2A and 100% in FIG. 2B. Results are shown for both pressurized oxygen gas and pressurized nitrogen gas. The nitrogen gas serves as a control. The thermogravimetric profile shows weight of sample versus temperature over a temperature range of 30° C. to 400° C. In FIG. 2A, the thermogravimetric profile is statistically different for the pressurized oxygen as compared with the pressurized nitrogen. For example in FIG. 2A, at 300° C. the weight reduction is 1.08% for the pressurized oxygen and only 0.34% for the pressurized nitrogen. In FIG. 2B, there is no statistically significant difference between the thermogravimetric profiles for the pressurized oxygen and the pressurized nitrogen. For example in FIG. 2B, at 300° C. the weight reduction is 0.43% for the pressurized oxygen and 0.37% for the pressurized nitrogen.

The preceding experimental results demonstrate that the pressurized oxygen reacted with phosphorus in the presence of moisture to generate phosphoric acid. Follow-up testing (electrical testing, material property testing, thermogravimetric analysis) showed that the properties of the molding compound had changed and that electrical shorts were generated. The electrical shorts were generated indirectly as a consequence of the changes in material properties, such as expansion of the material or creation of cracks in the material. In particular, the electrical shorts were generated through an electrolyte path as explained supra.

Based on the preceding experimental results, a method of testing and analysis of semiconductor packages subjected to a pressurized oxygen, with nitrogen or another inert gas serving as a control, may be used to assess the stability of such semiconductor packages in a sustained oxygen environment, as described next.

Test Environment, Methodology, and Analysis of the Present Invention

Figure 3:
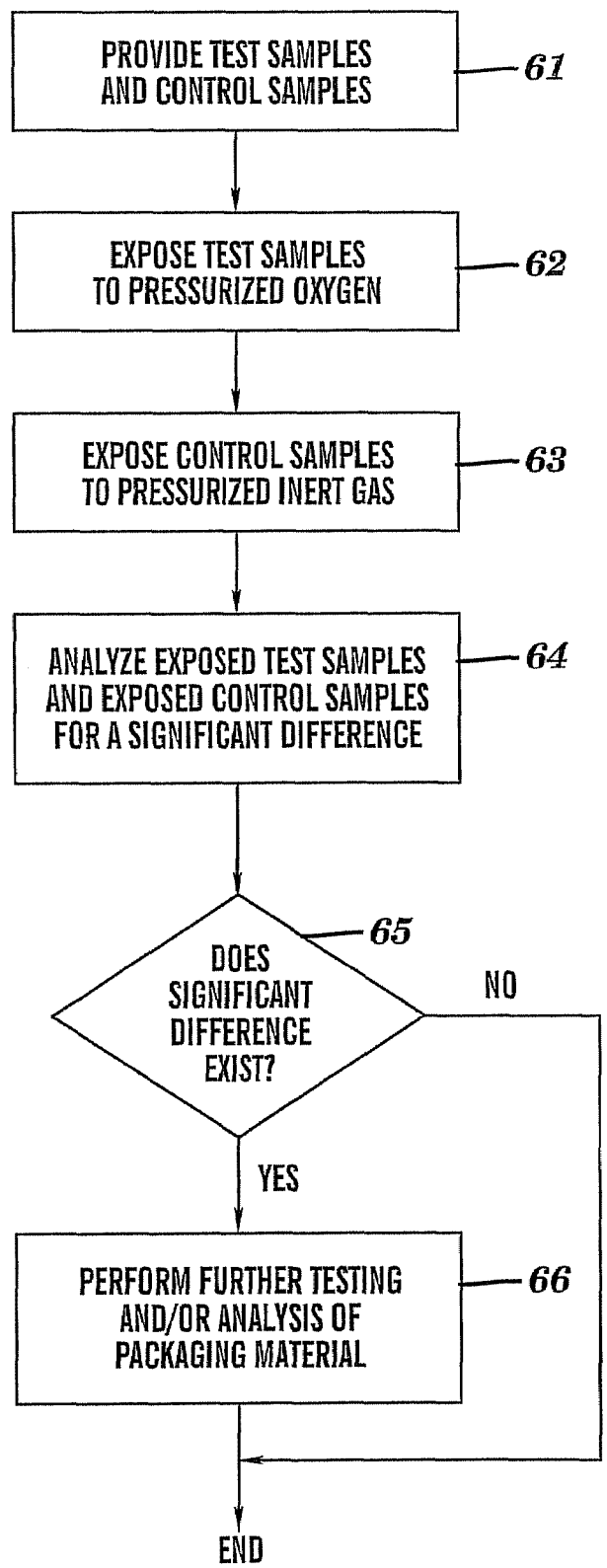
FIG. 3 is a flow chart depicting a method of testing and analyzing a semiconductor package material for stability in a sustained oxygen environment, in accordance with embodiments of the present invention.

FIG. 3 is a flow chart depicting steps 61-66 which describe a process or method of testing and analyzing a semiconductor package material for stability in a sustained oxygen environment, in accordance with embodiments of the present invention. The stability includes mechanical stability, electrical stability, and chemical stability.

Step 61 provides one or more substantially identical test samples, each comprising the semiconductor package material containing a molding compound. The test samples will be subjected to pressurized oxygen, as will be described infra in conjunction with step 62. Step 61 also provides one or more substantially identical control samples, each comprising the semiconductor package material. The control samples will be subjected to a pressurized inert gas (e.g., nitrogen, argon, etc.), as will be described infra in conjunction with step 63. Each of the test samples is substantially identical to each of the control samples. Two samples are said to be substantially identical if the two samples differ only in a minor respect which cannot be reasonably expected to impact the stability of the semiconductor package material.

The preceding description of step 61 may be more abstractly described as providing N substantially identical samples such that N is a positive integer of at least 2. Each of the N samples comprises the semiconductor packaging material containing a molding compound. T samples of the N samples are test samples and C samples of the N samples are control samples, wherein T and C are positive integers such that T+C=N. For example, if T=10 and C=2 then N=12; i.e., there are 12 substantially identical samples of which 10 are test samples and 2 are control samples. In an embodiment, the N samples are essentially identical, which is a special case of the N samples being substantially identical.

In an embodiment, the N samples each comprise a semiconductor package that includes the semiconductor packaging material. The semiconductor package material includes a molding compound. In another embodiment, the N samples each comprise a portion of a semiconductor package, wherein the portion is less than the entire semiconductor package, and wherein the portion includes the semiconductor packaging material. As an example, the portion may consist of one or more cured raw materials containing the molding compound. In yet another embodiment, the N samples each comprise a coupon of the one or more cured raw materials containing the molding compound.

Inasmuch as the experimentation described supra relates to molding compounds containing phosphorus (i.e., red phosphorus), the molding compound in the semiconductor package material tested and analyzed in accordance with the present invention may include phosphorus (e.g., red phosphorus). However, the scope of the present invention includes any molding compound found in semiconductor packaging materials, including molding compounds not containing phosphorus.

In step 62, the T test samples are exposed to a pressurized gas during a time period $\tau$, wherein $\tau$ is at least about 12 hours. $\tau$ may have any value of at least 12 hours such as, inter alia, D days plus H hours+M minutes+S seconds, wherein D is a non-negative integer, wherein H is a positive integer less than 24, M is a positive integer less than 60, and S is a positive integer less than 60 (e.g., D=0, 1, 2, 3, 4, >4, etc.; H=1, 2, 4, 8, 12, >12, etc; M=10, 25, 40, >40, etc.; S=10, 25, 40, >40 etc.). If D=0 then H must be at least about 12.

The pressurized gas includes oxygen gas and may also include one or more inert gases. In an embodiment, the pressurized gas is about 100% oxygen gas. For times t during $0 \leq t \leq \tau$, the oxygen gas has a partial pressure $P(t)$ of at least $P_1$, wherein $P_1$ about 15 psi. Generally, the pressurized gas has a total pressure $P_{TOT}(t)$ such that $P_{TOT}(t) \geq P(t)$. In various embodiments, $P_1$ is at least about 15, 100, 300, 500, 1000, etc. In various embodiments, $P(t)$ and/or $P_{TOT}(t)$ may not exceed about 1500 psi, 1800 psi, 2000 psi, 2500 psi, 3000 psi>3000 psi, etc. $P(t)$ and/or $P_{TOT}(t)$ may be approximately constant (e.g., $P_2$ is about equal to $P_1$ if $P(t)$ is approximately constant). Alternatively $P(t)$ and/or $P_{TOT}(t)$ may be variable in time (i.e., $dP(t)/dt \neq 0$ and/or $dP_{TOT}(t)/dt \neq 0$ within $0 \leq t \leq \tau$) with any time dependence (e.g., monotonically increasing, monotonically decreasing, oscillatory, etc.).

Also during $0 \leq t \leq \tau$ the oxygen gas has a temperature T(t) satisfying $T_G - \Delta T_2 \leq T(t) \leq T_G - \Delta T_1$. $\Delta T_1$ and $\Delta T_2$ satisfy $0 < \Delta T_1 \leq \Delta T_2$ for glass transition temperature $T_G$ of the molding compound. The minimum temperature $T_G - \Delta T_2$ of T(t) is at least about 20° C. In various embodiments, $T_G - \Delta T_2$ is at least about 20° C., 35° C., 50° C., 75° C., 85° C., >85° C., etc. T(t) is constrained to be below $T_G$ in order to reduce or minimize the chance of stress relief from material properties that exist in the molding compound at $T_G$ or above. T(t) may be approximately constant (i.e., $\Delta T_1$ is about equal to $\Delta T_2$). Alternatively T(t) may be variable in time (i.e., dT(t)/dt≠0 within $0 \leq t \leq \tau$) with any time dependence (e.g., monotonically increasing, monotonically decreasing, oscillatory, etc.).

Moisture is typically present under normal operating conditions and is thus made available during the oxygen exposure of the T test samples to react with any reaction products that might be produced during the oxygen exposure. Accordingly, during $0 \leq t \leq \tau$, the T test samples are exposed to moisture having a relative humidity H(t) such that $H_1 \leq H(t) \leq H_2$, wherein $H_1 \geq 0\%$ and $H_2 \leq 100\%$. H(t) may be approximately constant (i.e., $H_2$ is about equal to $H_1$) (e.g., H(t) is about equal to 0%, 25%, 50%, 80%, 100%, etc). Alternatively H(t) may be variable in time (i.e., dH(t)/dt≠0 within $0 \leq t \leq \tau$) with any time dependence (e.g., monotonically increasing, monotonically decreasing, oscillatory, etc.).

Figure 4:
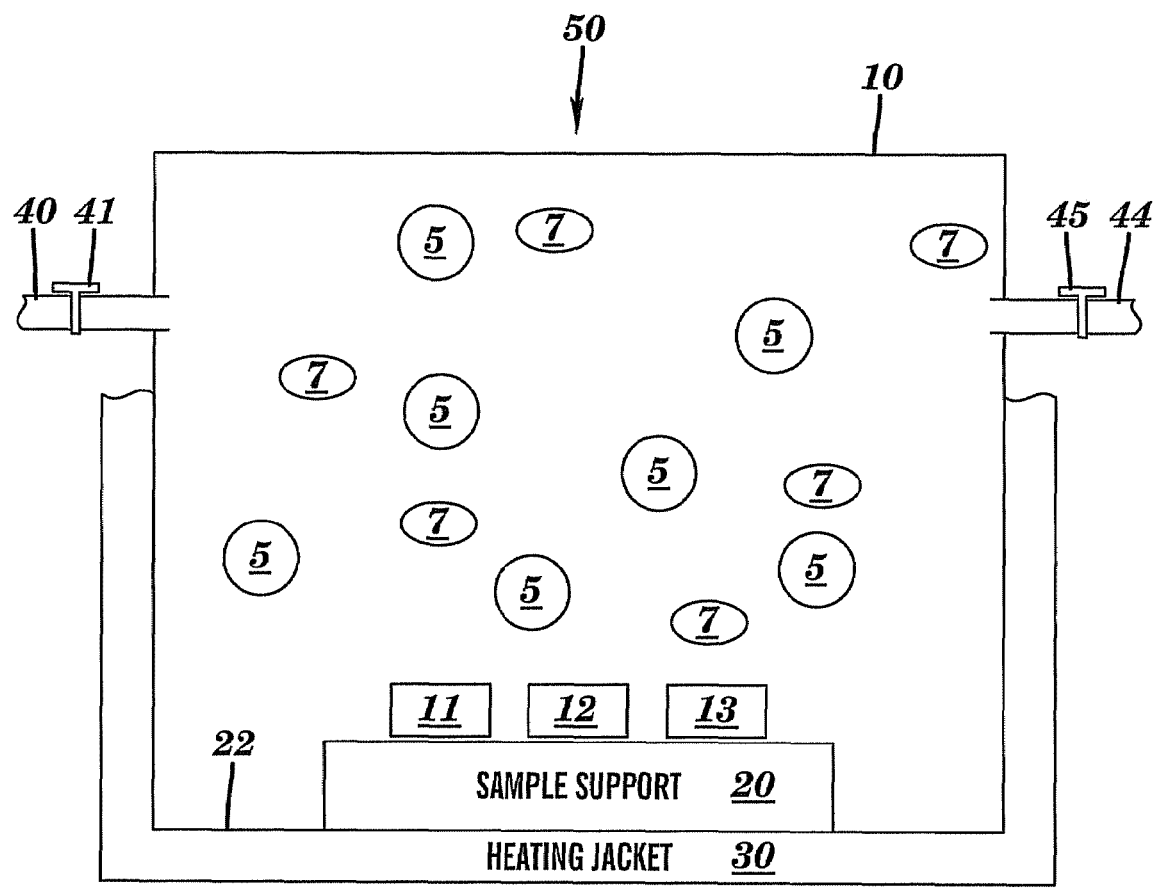
FIG. 4 depicts a test chamber containing semiconductor package samples and a pressurized gas, in accordance with embodiments of the present invention.

During the exposure to the pressurized oxygen, the T test samples are in an open vial and the vial as well as the pressurized oxygen are within a closed, heated chamber as is described infra in conjunction with FIG. 4.

Subtle oxygen reactions can change the properties of the molding compound over time and could result in failure of the semiconductor package as explained supra. Accordingly, a purpose of using a higher oxygen partial pressure and temperature for the testing of the present invention than the oxygen partial pressure and temperature existing under ambient atmospheric conditions is to accelerate any instability effects in the molding compound that might occur as a consequence of prolonged exposure to oxygen.

In step 63, the C control samples are exposed during times t for a time period $\tau'$ to a pressurized inert gas (e.g., nitrogen, argon, etc.) having a pressure P'(t) and a temperature of T'(t) at a relative humidity H'(t). The C control samples are not exposed to oxygen gas while being exposed to the pressurized inert gas. A common time interval exists for times t during which both the pressurized gas comprising oxygen and the pressurized inert gas are being exposed by the respective exposing steps. During said common time interval: P'(t)≧P(t) or P'(t) does not substantially differ from P(t), T'(t)≧T(t) or T'(t) does not substantially differ from T(t), and H'(t)≧H(t) or H'(t) does not substantially differ from H(t).

As an alternative embodiment, the condition of "P'(t) does not substantially differ from P(t)" may be replaced by the more stringent condition of "P'(t)≧$P_{TOT}$(t) or P'(t) does not substantially differ from $P_{TOT}$(t)" (e.g., in situations in which the samples may be adversely affected by total pressure).

To be explained next is the meaning herein, including in the claims, of "does not substantially differ from" in the following expressions: "P'(t) does not substantially differ from P(t)", "T'(t) does not substantially differ from T(t)", "H'(t) does not substantially differ from H(t)".

Consider the expression: "P'(t) does not substantially differ from P(t)". To determine whether P'(t) differs substantially from P(t), one must analyze P(t) and P'(t) comparatively as pressure profiles versus time over the entire time domains of $\tau$ and $\tau'$, respectively. The analysis is not based exclusively on a comparison between P(t) and P'(t) at each point in time. For example, consider the T test samples and the C control samples being exposed for about 5 days to pressurized oxygen gas at 1800 psi of pressure and to the pressurized inert gas at 1800 psi, respectively, except that during 5 minutes of the 5 days of exposure the pressure P'(t) of the pressurized inert gas is ramped down to about 300 psi and then ramped back up to about 1800 psi. In said example, the pressures P(t) and P'(t) do not differ substantially from each other because 5 minutes is only about 0.07% of the 5 days, and said deviation between P(t) and P'(t) is insignificant (e.g., said deviation between P(t) and P'(t) has no more than a negligible effect on the difference in properties between the T test samples and the C control samples at the end of the exposure periods $\tau$ and $\tau'$).

In summary, the analysis should include looking at P(t) and P'(t) (or alternatively $P_{TOT}$(t) and P'(t) as explained supra) at each point in time, and if P(t) and P'(t) (or $P_{TOT}$(t) and P'(t)) do not substantially differ at each point in time, then P'(t) is said to not substantially differ from P(t) (or from $P_{TOT}$(t)). However, if P(t) and P'(t) (or $P_{TOT}$(t) and P'(t)) substantially differ from each other at one or more points in time, then the analysis should determine whether said deviation between P(t) and P'(t) (or between $P_{TOT}$(t) and P'(t)) is insignificant as in the preceding example having the 5 minutes of deviation in P'(t).

The preceding discussion of the meaning of "does not substantially differ from" in the expression of "P'(t) does not substantially differ from P(t)" applies analogously to the meaning of the expressions "P'(t) does not substantially differ from $P_{TOT}$(t)", "T'(t) does not substantially differ from T(t)" and "H'(t) does not substantially differ from H(t)".

During the exposure to the pressurized inert gas, the C control samples are in an open vial and the vial as well as the pressurized inert gas are within a closed, heated chamber as is described infra in conjunction with FIG. 4.

Consider next a comparison between the exposure period $\tau$ of the T test samples to the pressurized gas (including oxygen) and the exposure period $\tau'$ of the C control samples to the pressurized inert gas. Consider the following useful embodiments: $\tau'$ is about equal to $\tau$, $\tau'$ does not substantially differ from $\tau$, $\sigma' < \sigma$, and $\tau' > \tau$.

The embodiment of "$\tau'$ is about equal to $\tau$" is characterized by a strict level of experimental control for utilizing about the same exposure period for the C control samples as for the T test samples.

The embodiment of "$\tau'$ does not substantially differ from $\tau$" is characterized by substantially a same level of experimental control for utilizing substantially the same exposure period for the C control samples as for the T test samples.

The embodiment of $\tau' < \tau$ facilitates a conservative test in which the T test samples are exposed to the pressurized gas (including oxygen) for a longer period of time than are the C control samples exposed to the pressurized inert gas. For said embodiment of $\tau' < \tau$, if the measured properties of the T test samples and the C control sample do not significantly differ following the respective exposure periods of $\tau$ and $\tau'$, then the test results conservatively show that the exposure of the T test samples to the pressurized gas (including oxygen) was negative with respect to said differences in the measured properties. However, if a measured property of the T test samples and the C control sample significantly differs following the respective exposure periods of $\tau$ and $\tau'$, then the test results are indicative of a need for further testing or analysis to differentiate between: 1) the effect of the exposure of the T test samples to the pressurized gas (including oxygen); and 2) the effect of the differential between $\tau'$ and $\tau$.

The embodiment of $\tau' > \tau$ facilitates an economical test in which the T test samples are exposed to the pressurized gas (including oxygen) for a shorter period of time than are the C control samples exposed to the pressurized inert gas. For said embodiment of $\tau'>\tau$, if a measured properties of the T test samples and the C control sample significantly differ following the respective exposure periods of $\tau$ and $\tau'$ then the test results show, in an economically short period of exposure, that the exposure of the T test samples to the pressurized gas (including oxygen) causes changes in said measured properties. However, if the measured properties of the T test samples and the C control sample do not significantly differ following the respective exposure periods of $\tau$ and $\tau'$, then the test results are indicative of a need for further testing or analysis to determine whether the exposure of the T test samples to the pressurized gas (including oxygen) causes changes in said measured properties.

Although FIG. 3 shows step 63 being performed after step 62 is performed, step 63 may alternatively be performed before step 62 is performed.

Since the inert gas is not expected to chemically react with the molding compound, step 63 serves the purpose of being a control step to provide a benchmark against which the results of the oxygen pressurization of step 62 may be compared. A significant difference between the test samples and the control samples following execution of steps 62 and 63 is suggestive of the possibility that the semiconductor packaging material being tested is unstable in a prolonged exposure to oxygen under normal operating conditions.

Accordingly after the T test samples and the C control samples have been exposed, step 64 analyzes the T oxygen-exposed test samples and the C inert gas-exposed control samples. The analysis of step 64 includes: measuring at least one characteristic common to the C control samples and the T test samples; and determining whether there exists at least one significant difference between the at least one characteristic of the T test samples and the at least one characteristic of the C control samples. If T>1 and/or C>1, which may be equivalently expressed as N>2, determining whether there exists said at least one significant difference may comprises performing a statistical analysis of the at least one characteristic of the C control samples and/or the T test samples. Step 65 is a decision block which determines the next action based on whether said at least one significant difference has been determined to exist. If at least one significant difference is determined not to exist then the process ends. If at least one significant difference not determined to exist then step 66 is next executed, followed by ending the process. Step 66 performs further testing, analysis, or testing and analysis of the semiconductor packaging material to more definitively assess the likelihood of the semiconductor packaging material being unstable in a prolonged exposure to oxygen. Thus, the method described by the flow chart of FIG. 3 may serve as a screening process to screen out those semiconductor packaging materials which are candidates for being unstable when subjected to continuous, prolonged exposure to oxygen under normal operating conditions.

The measuring in step 64 may include any known measuring technique known to one of ordinary skill in the art for determining test and control sample characteristics which, in light of the experimental results discussed supra, are relevant to assessing the stability of the semiconductor packaging material. Two such measuring techniques employed by the present inventors are: ion chromatography and thermogravimetric analysis.

Ion chromatography identifies and quantifies ionic residues on the T test samples and the C control samples, as exemplified by the discussion supra of FIG. 1. Following the exposure of the samples to the pressurized oxygen or to the pressurized inert gas, a quantity of deionized water (e.g., 25 milliliters) is added to the vial containing the samples and the samples are soaked in the ionized water for a sufficient period of time (e.g., 24 hours) to collect measurable ionic species; then the ionized water is analyzed by ion chromatography to determine the type and concentration of ions present in the deionized water.

Using the ion chromatography, of particular interest for phosphorus-containing molding compounds is the phosphate ion generated by reaction of phosphorus and oxygen in the presence of water. As explained supra in conjunction with FIG. 1, the chloride ion may be of additional interest even though the detection of chloride ions may be a consequence of an oxygen reaction with phosphorus and water such that chlorine or the chloride ion does not directly participate in a chemical reaction involving oxygen. Other ions of interest may include, inter alia, fluoride ions, sulfate ions, nitrate ions, etc. The particular ions of interest depends on the particular packaging material at issue.

In reviewing the ion chromatography data for a significant difference between the detected ions of the T test samples and the C control samples, the table of FIG. 1 shows such a significant difference in both phosphate ions and chloride ions for package types 1-5 and no significant difference for package types 6-10. Thus based on the ion chromatography results of FIG. 2A, packages 1-5 are candidates for being unstable when subjected to continuous, prolonged exposure to oxygen under normal operating conditions, while packages 6-10 are not candidates for being unstable when subjected to continuous, prolonged exposure to oxygen under normal operating conditions.

Thermogravimetric analysis measures weight changes in each sample as a function of temperature, as exemplified by the discussion supra of FIGS. 2A-2B where the temperature range is 30° C. to 400° C. In FIG. 2A, the thermogravimetric profiles reveal a significant difference between the test sample that had been subject to oxygen pressurization and the control sample that had been subjected to nitrogen pressurization. Thus based on the thermogravimetric profiles of FIG. 2A, the packaging material of the test sample in FIG. 2A is a candidate for being unstable when subjected to continuous, prolonged exposure to oxygen under normal operating conditions. In FIG. 2B, the thermogravimetric profiles did not reveal a significant difference between the test sample that had been subject to oxygen pressurization and the control sample that had been subjected to nitrogen pressurization. Thus based on the thermogravimetric profiles of FIG. 2B, the packaging material of the test sample in FIG. 2A is not a candidate for being unstable when subjected to continuous, prolonged exposure to oxygen under normal operating conditions.

FIG. 4 depicts a test environment 50 for implementing step 62 or 63 of FIG. 3. In FIG. 4, the test environment 50 comprising a chamber 10 containing semiconductor package samples 11-13 on a support 20, pressurized gas 5, moisture 7, and a heater 30, in accordance with embodiments of the present invention. Alternatively, the samples 11-13 may be positioned directly on the bottom surface 22 of the chamber 10 instead of on the support 20. The pressure of the gas 5 is controlled by gas inlet line 40 with valve 41 and gas outlet line 44 with valve 45. If the samples 11-13 are test samples, then the gas 5 comprises oxygen as in step 62 of FIG. 3. If the samples 11-13 are control samples, then the gas 5 is an inert gas (e.g., nitrogen, argon, etc.) as in step 62 of FIG. 3. In FIG. 4, the temperature of the gas in the chamber is controlled by the heating jacket 30 or any other means for heating the chamber 10. The moisture 7 may be set at any desired relative humidity by any means or method known to a person of ordinary skill in the art such as a source of water within the chamber (not shown), or a combination of water and various salts, vaporized to generate the moisture 7. The chamber 10 may be evacuated by a vacuum pump (not shown). Instrumentation (not shown) for measuring the gas pressure, gas temperature, and relative humidity in the chamber 10 may also be present.

As described herein in relation to the present invention, the testing using pressurized oxygen at elevated temperature accelerates changes in semiconductor packaging material in order to simulate actual changes that are expected to occur in the semiconductor packaging material under prolonged exposure to oxygen under normal operating conditions. The testing and subsequent analysis of the test data can be used to rule out future concerns associated with stability of packaging materials in an oxygen environment, or as a screening tool to trigger a need for further investigation of the stability of the packaging materials in light of oxidation reaction concerns. Said testing and analysis can be additionally used to evaluate parts prepared from the same molding compound but under different molding conditions, Variations in molding conditions or in packaging design could result in increased or decreased failure rate, even for the same molding compound. Said testing and analysis can also be used to compare the stability of different packaging materials, including different packaging materials having similar or different chemistries, or having been generated by similar or different fabrication methods, or having been packaged or otherwise formed within its module or package by a similar or different packaging process. To improve an evaluation of the probability of failure of the semiconductor package, said testing and analysis may be used in combination with conventional reliability tests including tests which induce mechanical stresses, thermal stresses, excess moisture, etc., and conventional tests for mechanical faults, electrical faults, etc.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method of testing a semiconductor packaging material containing a molding compound, said method comprising the steps of:

providing N substantially identical samples such that N is a positive integer of at least 2, wherein each of the N samples comprises the semiconductor packaging material, wherein the semiconductor packaging material comprised by the N samples comprises one or more cured raw materials containing the molding compound, wherein T samples of the N samples are test samples, wherein C samples of the N samples are control samples, and wherein T and C are positive integers such that T+C=N;

exposing during a time period $\tau$ the T test samples to a pressurized gas having a total pressure $P_{TOT}(t)$, said pressurized gas comprising oxygen gas, wherein for times t during $0 \leq t \leq \tau$ the oxygen gas has a partial pressure $P(t)$ of at least $P_1$ and a temperature $T(t)$ satisfying $T_G - \Delta T_2 \leq T(t) \leq T_G - \Delta T_1$ such that $0 < \Delta T_1 \leq \Delta T_2$ for glass transition temperature $T_G$ of the molding compound, wherein during $0 \leq t \leq \tau$ the T test samples are exposed to moisture having a relative humidity $H(t)$ such that $H_1 \leq H(t) \leq H_2$, wherein $H_1 \geq 0\%$ and $H_2 \leq 100\%$, wherein $\tau$ is at least about 12 hours, wherein $P_1$ is about 15 psi, and wherein $T_G - \Delta T_2$ is at least about 20° C.; and exposing the C control samples during times t for a time period $\tau'$ to a pressurized inert gas having a pressure $P'(t)$ and a temperature of $T'(t)$ at a relative humidity $H'(t)$, wherein a common time interval exists for times t during which both the pressurized gas comprising oxygen and the pressurized inert gas are being exposed by the respective exposing steps, wherein during said common time interval: $P'(t) \geq P(t)$ or $P'(t)$ does not substantially differ from $P(t)$, $T'(t) \geq T(t)$ or $T'(t)$ does not substantially differ from $T(t)$, and $H'(t) \geq H(t)$ or $H'(t)$ does not substantially differ from $H(t)$.

2. A method of testing and analyzing a semiconductor packaging material containing a molding compound for stability of the semiconductor packaging material in a sustained oxygen environment, said method comprising the steps of:

providing N substantially identical samples such that N is a positive integer of at least 2, wherein each of the N samples comprises the semiconductor packaging material, wherein the semiconductor packaging material comprised by the N samples comprises one or more cured raw materials containing the molding compound, wherein T samples of the N samples are test samples, wherein C samples of the N samples are control samples, and wherein T and C are positive integers such that T+C=N;

exposing during a time period $\tau$ the T test samples to a pressurized gas having a total pressure $P_{TOT}(t)$, said pressurized gas comprising oxygen gas, wherein for times t during $0 \leq t \leq \tau$ the oxygen gas has a partial pressure $P(t)$ of at least $P_1$ and a temperature $T(t)$ satisfying $T_G - \Delta T_2 \leq T(t) \leq T_G - \Delta T_1$ such that $0 < \Delta T_1 \leq \Delta T_2$ for glass transition temperature $T_G$ of the molding compound, wherein during $0 \leq t \leq \tau$ the T test samples are exposed to moisture having a relative humidity $H(t)$ such that $H_1 \leq H(t) \leq H_2$, wherein $H_1 \geq 0\%$ and $H_2 \leq 100\%$, wherein $\tau$ is at least about 12 hours, wherein $P_1$ is about 15 psi, and wherein $T_G - \Delta T_2$ is at least about 20° C.;

exposing the C control samples during times t for a time period $\tau'$ to a pressurized inert gas having a pressure $P'(t)$ and a temperature of $T'(t)$ at a relative humidity $H'(t)$, wherein a common time interval exists for times t during which both the pressurized gas comprising oxygen and the pressurized inert gas are being exposed by the respective exposing steps, wherein during said common time interval: $P'(t) \geq P(t)$ or $P'(t)$ does not substantially differ from $P(t)$, $T'(t) \geq T(t)$ or $T'(t)$ does not substantially differ from $T(t)$, and $H'(t) \geq H(t)$ or $H'(t)$ does not substantially differ from $H(t)$;

wherein after said exposing the T test samples and the C control samples, the method further comprises:

measuring at least one characteristic common to the C control samples and the T test samples;

ascertaining that there exists at least one significant difference between the at least one measured characteristic of the T test samples and the at least one characteristic of the C control samples; and responsive to said ascertaining, designating the semiconductor packaging material as being unstable and performing further testing, analysis, or testing and analysis of the semiconductor packaging material.

3. The method of claim 2, wherein measuring the at least one characteristic of the C control samples and the T test samples includes performing ion chromatography on the C control samples and the T test samples to determine ions and their concentrations present in the C control samples and the T test samples, and wherein said performing ion chromatography determines different ion concentrations in the T test samples than in the C control samples.

* * * * *